(12) United States Patent
Jordan et al.

(10) Patent No.: US 6,423,342 B1
(45) Date of Patent: Jul. 23, 2002

(54) PROCESS FOR THE PREPARATION OF A SOLID PHARMACEUTICAL DOSAGE FORM

(75) Inventors: Andrew William Jordan, Swindon; Joy Elaine Saunders, Faringdon; Patrick Kearney, Swindon, all of (GB)

(73) Assignee: R. P. Scherer Corporation, St. Petersburg, FL (US)

( * ) Notice: Subject to any disclaimer, the term of this patent is extended or adjusted under 35 U.S.C. 154(b) by 0 days.

(21) Appl. No.: 09/305,080

(22) Filed: May 4, 1999

Related U.S. Application Data

(63) Continuation-in-part of application No. 08/894,765, filed as application No. PCT/GB96/00483 on Mar. 1, 1996, now abandoned.

(30) Foreign Application Priority Data

Mar. 2, 1995 (GB) .............................................. 9504201

(51) Int. Cl.⁷ ............................ A61K 9/10; A61K 9/14; A61K 31/137; A61P 25/16
(52) U.S. Cl. ..................... 424/484; 424/489; 514/655
(58) Field of Search ..................... 424/484, 485–488, 424/499–502; 514/655

(56) References Cited

U.S. PATENT DOCUMENTS

| | | | |
|---|---|---|---|
| 4,963,367 A | * | 10/1990 | Ecanow |
| 5,079,018 A | | 1/1992 | Ecanow |
| 5,298,261 A | * | 3/1994 | Pebley et al. |

FOREIGN PATENT DOCUMENTS

| | | |
|---|---|---|
| EP | 0 084 705 | 11/1982 |
| FR | 2 366 835 | 10/1977 |
| GB | 1 548 022 | 10/1976 |
| GB | 2 111 423 A | 11/1982 |
| WO | WO 91/09591 | 7/1991 |
| WO | WO 03/12769 | 7/1993 |
| WO | WO 03/23017 | 11/1993 |

OTHER PUBLICATIONS

US 5,120,549, 06/1992, Gole et al. (withdrawn)

* cited by examiner

*Primary Examiner*—Edward J. Webman
(74) *Attorney, Agent, or Firm*—Donald O. Nickey; Robert W. Diehl; Wallenstein & Wagner

(57) ABSTRACT

A process for the preparation of a solid pharmaceutical dosage form comprising a carrier and, as active ingredient, a compound which exists, in solution, in an equilibrium between a free acid or free base form and a salt form, and for which there is a difference in volatility between the free acid or free base form and the salt form. The process includes the steps of solidifying a mixture of the compound and carrier in a solvent, and subsequently removing the solvent from the solidified mixture. A pH modifier is added to the mixture prior to solidification to shift the equilibrium to favor the less volatile form of the active ingredient.

8 Claims, No Drawings

PROCESS FOR THE PREPARATION OF A SOLID PHARMACEUTICAL DOSAGE FORM

RELATED APPLICATIONS

This application is a continuation-in-part of U.S. patent application Ser. No. 08/894,765, filed Nov. 6, 1997, now abandoned, which is the nationalization of PCT/GB96/00483, filed Mar. 1, 1996, which is based on GB 9504201.6, filed Mar. 2, 1995.

TECHNICAL FIELD

This invention relates to a process for the preparation of a solid pharmaceutical dosage form and solid pharmaceutical dosage forms produced by this process.

PREFERRED EMBODIMENT

Many solid pharmaceutical dosage forms, especially fast-dispersing dosage forms, are manufactured by processes which involve the steps of solidifying, for instance by freezing, a mixture of the active ingredient and a carrier in a solvent and subsequently removing the solvent from the solidified mixture by sublimation or some other means. However, some active ingredients are susceptible to the means used for removing the solvent, such as sublimation, or evaporation, during such manufacturing processes resulting in a loss of potency in the final product. Moreover, active ingredients which have been utilized in such manufacturing processes tend to adopt an amorphous structure which is chemically less stable than the crystalline form and this can contribute to a further loss of potency during manufacture and storage of the dosage form. Accordingly it is desirable to find a method of stabilizing such susceptible active ingredients during such manufacturing processes.

It is well known that many pharmaceutically active compounds are weak acids or weak bases. Accordingly, in solution, an equilibrium is established between the free acid and the salt form or the free base and the salt form. Moreover, there is often a considerable difference in volatility between the free acid or free base and the salt form. It has therefore been found that, by adjusting the pH of the solution containing the active ingredient, the equilibrium can be shifted to favor the less volatile form of the active ingredient whether it be the free acid or base or the salt form.

According to a first aspect of the present invention there is therefore provided a process for the preparation of a solid pharmaceutical dosage form comprising a carrier and, as active ingredient, a compound which is susceptible to either sublimation or evaporation during the preparation process, which process includes the steps of solidifying a mixture of the compound and carrier in a solvent and subsequently removing the solvent from the solidified mixture, characterized in that a pH modifier is added to the mixture prior to solidification.

Preferably, the solid pharmaceutical dosage form is a solid, fast-dispersing dosage form. Such fast-dispersing dosage forms typically disintegrate within 1 to 10 seconds of being placed in the oral cavity and many different examples of such dosage forms are already known.

For instance, U.S. Pat. No. 5,120,549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast-dispersing matrix.

U.S. Pat. No. 5,079,018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. W093/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

The term "fast-dispersing dosage form" therefore encompasses all the types of dosage form described in the preceding paragraphs. However, it is particularly preferred that the fast-dispersing dosage form is of the type described in U.K. Patent No. 1548022, that is, a solid fast-dispersing dosage form comprising a network of the active ingredient and a water-soluble or water-dispersible carrier which is inert towards the active ingredient, the network having been obtained by subliming solvent from a composition in the solid state, that composition comprising the active ingredient and a solution of the carrier in a solvent.

One example of an active ingredient which is susceptible to evaporation during such manufacturing processes is selegiline ((−)-N,α-dimethyl-N-2-propynylphenethylamine) which is useful in the treatment of Parkinson's disease and it is therefore particularly preferred that the active compound is selegiline or an acid-addition salt thereof, especially the hydrochloride. Another suitable active ingredient is nicotine.

Clinical studies have shown that 23–52% of patients with Parkinson's disease have swallowing difficulties and many such patients tend to dribble. Accordingly, it is particularly desirable to be able to administer selegiline in a fast-dispersing dosage form which will disintegrate rapidly in the mouth thereby minimizing the above problems. Fast-dispersing dosage forms of selegiline may be prepared by first freezing unit doses of an aqueous dispersion of the drug and then removing the water by sublimation or some other suitable means. When in the solution phase, the selegiline will be in an equilibrium between the salt form and the free base. However, the free base of selegiline is a volatile oil which can evaporate during the manufacturing process or from the finished product. Accordingly, it is desirable in this case to shift the equilibrium towards the salt form by lowering the pH of the solution using a suitable pH modifier.

Suitable pH modifiers for lowering the pH of a mixture are generally acids, especially organic acids. Preferred acids include citric acid, tartaric acid, phosphoric acid, hydrochloric acid and maleic acid. Of these, citric acid is particularly preferred.

Clearly, there will be some cases where it will be desirable to increase the pH of the solution to favor the less volatile component. Suitable pH modifiers in this case are generally bases. Suitable inorganic bases include sodium hydroxide, potassium hydroxide and carbonates and bicarbonates of sodium and potassium and other suitable elements. Suitable organic bases include propanolamine, ethanolamine, methylamine, dimethyl formamide, dimethylacetamide, diethanolamine, diisopropanolamine and triethanolamine.

Typically, the pH modifier will comprise 0.25 to 0.75% by weight, especially 0.4 to 0.6% by weight, of the initial mixture, that is, before removal of the solvent. If less than 0.25% by weight is present, the equilibrium may not be significantly affected. However, if more than 0.75% by weight is used, this can have a deleterious effect on the physical properties of the dosage form.

It is also known that the amorphous state of a compound is a high energy state. Accordingly, holding such a compound in the solidified state at a particular temperature may encourage the compound to transform to the chemically more stable, lower energy, crystalline state. It is therefore also preferred that the process of the invention comprises the further step of maintaining the solidified mixture within a specific temperature range for a specified period of time prior to removal of the solvent. The compound then retains the crystalline structure so produced throughout the remainder of the manufacturing process with the result that the finished product is chemically more stable than product which has not been treated in this way.

It is also envisaged that this further step could be advantageously performed in the absence of a pH modifier. According to a second aspect of the invention there is therefore provided process for the preparation of a solid pharmaceutical dosage form comprising a carrier and, as active ingredient, a compound which is susceptible to sublimation or evaporation during the preparation process, which process includes the steps of solidifying a mixture of the compound and carrier in a solvent and subsequently removing the solvent from the solidified mixture, characterized in that the solidified mixture is maintained within a specific temperature range for a specified period of time prior to removal of the solvent.

Preferably, the specific temperature range is from −15 to −25° C. It is also preferred that the specific period of time is not less than 1 hour, preferably at least 18 hours, more preferably, at least 24 hours and, especially, 24–30 hours.

According to another aspect of the invention there is provided a solid pharmaceutical dosage form whenever prepared by a process as described above.

In the case of the preferred type of fast-dispersing dosage form described above, the composition will preferably contain, in addition to the active ingredient, matrix forming agents and secondary components. Matrix forming agents suitable for use in the present invention include materials derived from animal or vegetable proteins such as the gelatins, dextrins and soy, wheat and psyllium seed proteins; gums such as acacia, guar, agar, and xanthan; polysaccharides; alginates, carboxymethyl-celluloses; carrageenans; dextrans; pectins; synthetic polymers such as polyvinylpyrrolidone; and polypeptide/protein or polysaccharide complexes such as gelatin-acacia complexes.

Other matrix forming agents suitable for use in the present invention include sugars such as mannitol, dextrose, lactose, and galactose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension. This is especially helpful in the case of active agents that are not sufficiently soluble in water and must, therefore, be suspended rather than dissolved.

Secondary components such as preservatives, antioxidants, surfactants, viscosity enhancers, coloring agents, flavoring agents, sweeteners or taste-masking agents may also be incorporated into the composition. Suitable coloring agents include red, black and yellow iron oxides and FD & C dyes such as FD & C blue No. 2 and FD & C red No. 40 available from Ellis & Everard. Suitable flavoring agents include mint, raspberry, liquorice, orange, lemon, grapefruit, caramel, vanilla, cherry and grape flavors and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

The invention is further illustrated by the following examples.

EXAMPLE 1

Preparation of a fast-dispersing dosage form (a) Preparation of Seleguine Hydrochloride 2.0% Dispersion Gelatin (720 g) and mannitol (540 g) were dispersed in a portion of purified water (15.73 kg) by mixing thoroughly in the bowl of a vacuum mixer. The remaining water (1.5 litres) was added under vacuum while mixing using an anchor stirrer. The mix was then heated to 40° C.±2° C. and homogenized for ten minutes. The mix was cooled down to room temperature. When cooled, a 4500 g portion of the mix was removed into a stainless steel vessel and glycine (360 g), aspartame (90 g), grapefruit flavor (54 g), Opatint yellow (54 g) and citric acid (90 g) were then added sequentially to this portion while homogenizing using a bench top homogenizer. The remainder of the mix was transferred into a second stainless steel vessel. Selegiline hydrochloride (360 g) was then added to the mix in the second vessel and the mix homogenized for ten minutes using a bench top mixer to dissolve the drug. Once dispersion of the coloring agent was complete, the portion of the mix removed to the first vessel was returned to the mixer bowl together with the homogenized mix from the second vessel. The combined mixes were then mixed for at least 20 minutes. The bulk dispersion was then homogenized to ensure that mixing was complete.

(b) Preparation of Selegiline Hydrochloride 5 mg Units 250 mg of the selegiline hydrochloride 2.0% dispersion formed in (a) above was dosed into each one of a series of pre-formed blister pockets having a pocket diameter of 12-mm. The blister laminate comprised 200 µm PVC/30 µm PE/PVDC 90 g per square metre. The product was frozen immediately in a liquid nitrogen freeze tunnel. The frozen product was then stored below −20° C. for a minimum of 24 hours prior to freeze-drying in a freeze drier using a drying temperature of +20° C. and a chamber pressure of 0.5 mbar. The freeze-dried units were then inspected for the presence of critical defects and the remainder of the batch sealed with lidding foil consisting of a paper/foil laminate (20 µm aluminium). Each blister was then coded with a batch number and over-wrapped in a preformed sachet by placing the blister in the sachet and sealing the open end of the sachet completely. Each sachet was then labeled with the product name, batch number, date of manufacture and suppliers name.

Each unit dosage form had the following composition:

| Ingredient | Weight (mg) | % by wt of composition |
| --- | --- | --- |
| *Purified Water SP/EP | 218.500 | 87.4 |
| Selegiline Hydrochloride | 5.000 | 2.0 |
| Gelatin EP/USNF | 10.000 | 4.0 |
| Mannitol EP/USP | 7.500 | 3.0 |
| Aspartame USNF | 1.250 | 0.5 |
| Grapefruit Flavor 502.106/A | 0.750 | 0.3 |
| Glycine USP | 5.000 | 2.0 |
| Citric Acid EP/USP | 1.250 | 0.5 |
| Opatint AD-22901 yellow | 0.750 | 0.3 |
|  | 250.000 | 100.0 |

*Signifies removed during the lyophilization process.

EXAMPLE 2

Effect of pH modification on stability

A series of dosage forms were manufactured as described in Example 1 but the quantity of citric acid used was varied. The dosage forms were then stored at 40° C./80% relative humidity for up to 7 weeks and the quantity of selegiline hydrochloride in these dosage forms was assayed at regular intervals. The results are given in Table 1 below.

TABLE 1

| Conc. of Citric Acid (% w/w) | Solution pH | Time = 0 | 1 week | 2 week | 4 week | 7 week |
| --- | --- | --- | --- | --- | --- | --- |
| 0 | 5.38 | 4.79 | 3.86 | 3.31 | 3.32 | — |
| 0.25 | 4.21 | 4.95 | 4.70 | 4.67 | 4.74 | 4.65 |
| 0.50 | 3.82 | 5.05 | 4.98 | 4.98 | 4.98 | 4.96 |
| 1.0 | 3.45 | 5.07 | 5.03 | 5.04 | 5.05 | 5.00 |
| 2.0 | 3.11 | 5.04 | 4.99 | 5.01 | 5.02 | 4.96 |

The progressively greater loss of initial potency with increasing pH can be attributed to the greater proportion of selegiline free base present which is lost during processing.

It can be seen that a minimum level of 0.5% citric acid is required to inhibit this loss of selegiline. This is also considered to be the optimum level as levels higher than 0.5% were found to have a deleterious effect on the physical properties of the dosage form, causing, for instance, cracking and base melting.

EXAMPLE 3

Effect of storage in frozen state

Two batches of selegiline fast-dispersing dosage forms manufactured as described in Example I were stored at different temperatures in the frozen state prior to drying. The results are given in Table 2 below.

TABLE 2

| Frozen Storage Temperature (° C.) | Assay Selegiline HCl (mg) | | | |
| --- | --- | --- | --- | --- |
| | Time = 0 | 1 week | 2 week | 4 week |
| −25 | 4.87 | 4.85 | 4.79 | 4.74 |
| −20 | 5.01 | — | 4.97 | 4.98 |

What is claimed is:

1. A process for the preparation of a solid, fast dispersing pharmaceutical dosage form comprising a carrier and, as active ingredient, selegiline or an acid-addition salt thereof, said process includes the steps of solidifying a mixture of selegiline or an acid-addition salt thereof and carrier in a solvent and subsequently removing the solvent from the solidified mixture, characterized in that a pH modifier which produces a less volatile form of the active ingredient is added to the mixture prior to solidification to shift the equilibrium to favor the less volatile form of the active ingredient.

2. A process according to claim 1, wherein the pH modifier lowers the pH of the mixture.

3. A process according to claim 1, wherein the pH modifier is selected from a group of compounds including citric acid, tartaric acid, phosphoric acid, hydrochloric acid, and maleic acid.

4. A process according to claim 1, wherein the pH modifier comprises 0.25 to 0.75% by weight of the mixture.

5. A process for the preparation of a solid pharmaceutical dosage form comprising a carrier and, as active ingredient, a compound which exit, in solution, in an equilibrium between a free acid or free base form and a salt form and for which there is a difference in volatility between the free acid or free base form and the salt form, which process includes the steps of solidifying a mixture of the compound and carrier in a solvent and subsequently removing the solvent from the solidified mixture, characterized in that the solidified mixture is maintained within a temperature range of −15 to −25° C. for a period of time of at least 18 hours prior to removal of the solvent.

6. A process according to claim 5, wherein the specified time period is at least 24 hours.

7. A solid pharmaceutical dosage form prepared by a process according to claim 1.

8. A process according to claim 1 wherein said pH modifier is selected from a group of compounds including sodium hydroxide, potassium hydroxide and carbonates and bicarbonates of sodium and potassium, propanolamine, ethanolamine, methylamine, dimethylformamide, dimethylacetamide, diethanolamine, diisopropylamine and triethanolamine.

* * * * *